United States Patent
Guimont et al.

(10) Patent No.: US 10,206,866 B2
(45) Date of Patent: Feb. 19, 2019

(54) NAIL COMPOSITIONS CONTAINING SILICONE-ORGANIC POLYMER HYBRID COMPOUND

(71) Applicant: L'ORÉAL, Paris (FR)

(72) Inventors: Aline Aude Guimont, Westfield, NJ (US); Chunhua Li, Hillsborough, NJ (US); Hy Si Bui, Piscataway, NJ (US); Christopher Michael MacNeill, Fanwood, NJ (US); Tsang-Min Huang, Scotch Plains, NJ (US); XianZhi Zhou, Millburn, NJ (US); Chaitrali Makarand Gothe, Santa Clara, CA (US); Ronni Lynn Weinkauf, Oradell, NJ (US)

(73) Assignee: L'ORÉAL, Paris (FR)

( * ) Notice: Subject to any disclaimer, the term of this patent is extended or adjusted under 35 U.S.C. 154(b) by 173 days.

(21) Appl. No.: 14/977,815

(22) Filed: Dec. 22, 2015

(65) Prior Publication Data

US 2017/0172899 A1 Jun. 22, 2017

(51) Int. Cl.
*A61K 8/895* (2006.01)
*A61Q 3/02* (2006.01)
*A61K 8/49* (2006.01)
*A61K 8/34* (2006.01)

(52) U.S. Cl.
CPC ............... *A61K 8/895* (2013.01); *A61K 8/34* (2013.01); *A61K 8/4973* (2013.01); *A61Q 3/02* (2013.01); *A61K 2800/594* (2013.01); *A61K 2800/81* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 5,725,882 A | 3/1998 | Kumar et al. | |
| 6,352,699 B1 * | 3/2002 | Mondet | A61K 8/042 424/401 |
| 2002/0010226 A1 * | 1/2002 | Lilley | A61K 8/8152 522/14 |
| 2006/0074187 A1 | 4/2006 | Stark et al. | |
| 2013/0263875 A1 | 10/2013 | Burgess et al. | |
| 2015/0139924 A1 | 5/2015 | Zhou et al. | |
| 2015/0306013 A1 | 10/2015 | Kergosien et al. | |

FOREIGN PATENT DOCUMENTS

WO WO 2011/069786 A2 6/2011
WO WO 2015/022438 2/2015

OTHER PUBLICATIONS

International Preliminary Report on Patentability and Written Opinion of the International Searching Authority dated Mar. 6, 2017 in PCT/US2016/063446 filed Nov. 23, 2016.
International Search Report dated Mar. 6, 2017 in PCT/US2016/063446 filed Nov. 23, 2016.

* cited by examiner

*Primary Examiner* — Nicole P Babson
(74) *Attorney, Agent, or Firm* — Oblon, McClelland, Maier & Neustadt, L.L.P.

(57) ABSTRACT

The invention relates to nail compositions comprising at least one silicone-organic polymer hybrid compound.

12 Claims, No Drawings

US 10,206,866 B2

NAIL COMPOSITIONS CONTAINING SILICONE-ORGANIC POLYMER HYBRID COMPOUND

FIELD OF THE INVENTION

The present invention relates to nail compositions comprising at least one silicone-organic polymer hybrid compound.

DISCUSSION OF THE BACKGROUND

UV gel compositions typically consist of a layer of basecoat for adhesion on the nails, one or more color coats to enhance the color, and a layer of topcoat for shine. Each coating needs to be cured with a UV Lamp or UV LED. A UV gel composition set is thus a system that typically contains base coat, color coat and top coat layers. The UV gel composition set's adhesion on the nail and the cohesion among the layers is so strong that it is difficult to remove such composition sets from nails. To remove such UV gel products from nails, it is usually required to soak nails with harsh solvent such as acetone for 20 minutes or more, followed by scraping the product off the nail. Frequent and/or prolonged use of such solvents in this manner and associated scraping can damage nails such as, for example, by making them dry and brittle. At the same time, the removal process is time-consuming.

Further, consumers come in contact with water several times a day during the course of the day, (for example, showers, hand washing, washing dishes, etc.). Such nail compositions sets are susceptible to damage by such frequent contact with water.

U.S. patent application publication no. 2013/0263875 relates to monophasic energy-curable solvent-free compositions which are formulated using at least one energy-curable resin and at least one film-former. Phthalic anhydride/glycerin/glycidyl decanoate copolymer is part of a laundry list of possible film formers in such compositions.

PCT patent application publication no. WO 2015/022438 relates to "novel plasticizers for nail varnish." Page 9 of the application refers to phthalic anhydride/glycerol/glycidyl decanoate copolymer in a laundry list of possible film formers.

It would be desirable to possess a UV gel product which has one or more of the following properties (preferably, all of the following properties): good water-resistance, good wear and/or good adhesion, without prolonging the amount of time needed for removal from nails. Also, it would be desirable to possess a UV gel product which does not include a basecoat and/or a topcoat, but which has good gloss/shine properties.

There remains a need for UV gel compositions which are safe and adhere well to nails, and which have some or all of the desired properties discussed above.

SUMMARY OF THE INVENTION

The present invention relates to a nail composition comprising at least one silicone-organic polymer hybrid compound.

The present invention also relates to a nail composition set comprising (1) at least one basecoat composition; and (2) at least one color coat composition comprising at least one silicone-organic polymer hybrid compound. Preferably, the nail composition set does not contain a topcoat.

The present invention also relates to a nail composition set comprising (1) at least one topcoat composition; and (2) at least one color coat composition comprising at least one silicone-organic polymer hybrid compound. Preferably, the nail composition set does not contain a basecoat.

The present invention also relates to a nail composition set consisting of at least one color coat composition comprising at least one silicone-organic polymer hybrid compound.

The present invention further relates to methods for making up and/or protecting nails comprising applying to the nails at least one nail composition comprising at least one silicone-organic polymer hybrid compound.

The present invention further relates to methods for making up and/or protecting nails comprising applying to the nails at least one nail composition set comprising (1) at least one basecoat composition; and (2) at least one color coat composition comprising at least one silicone-organic polymer hybrid compound. Preferably, the nail composition set does not contain a topcoat.

The present invention also relates to methods for improving gloss of a nail composition comprising (1) forming a nail composition comprising at least one silicone-organic polymer hybrid compound and (2) providing instructions (a) to apply the nail composition to nails to form an applied composition on the nails, (b) to subject the applied composition to ultraviolet (UV) or visible light radiation to form a cured composition on the nails, and (c) to apply at least one short chain alcohol to the cured composition on the nails, resulting in a glossy cured composition.

The present invention also relates to methods for improving gloss of a nail composition comprising (1) applying a nail composition comprising at least one silicone-organic polymer hybrid compound to nails to form an applied composition on the nails, subjecting the applied composition to ultraviolet (UV) or visible light radiation to form a cured composition on the nails, and applying at least one short chain alcohol to the cured composition on the nails, resulting in a glossy cured composition.

The present invention also relates to a kit for a nail composition set comprising at least one nail composition comprising at least one silicone-organic polymer hybrid compound.

The present invention also relates to a kit for a nail composition set comprising (1) at least one basecoat composition; and (2) at least one color coat composition comprising at least one silicone-organic polymer hybrid compound. Preferably, the nail composition set does not contain a topcoat.

It is to be understood that both the foregoing general description and the following detailed description are exemplary and explanatory only, and are not restrictive of the invention.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

"A" or "an" as used herein means "at least one."

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Adhesion" as used herein, refers to chemical and/or physical bonding between a coating and a substrate. Good adhesion between nail polish and nail surface should translate to good wear properties on consumers.

"Adhesive agent" or "adhesive" means a polymer that improves chemical and/or physical bonding between a coating and a substrate. In this invention, the adhesive agent improves bonding between compositions and the nail surface or other compositions.

"Removal" or "Easy removal" means the composition may be substantially removed with acetone or other organic solvents not limited to butyl acetate, isopropyl alcohol, ethanol, ethyl acetate, methyl acetate, methyl ethyl ketone, and mixtures thereof, followed by scraping of the composition from the nail.

"Film former", "film-forming polymer" or "film forming agent" or "co-film former" as used herein means a polymer or resin that leaves a film on the substrate to which it is applied, for example, after a solvent accompanying the film former has evaporated, absorbed into and/or dissipated on the substrate.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of solvents" means that non-aqueous solvents are preferably omitted (that is 0% by weight), but can be present in the composition at an amount of less than about 0.25% by weight, typically less than about 0.1% by weight, typically less than about 0.05% by weight, based on the total weight of the composition.

"Water free" or "free of water" herein means that water is preferably omitted (that is 0% by weight), but can be present in the composition at an amount of less than about 0.25% by weight, typically less than about 0.1% by weight, typically less than about 0.05% by weight, based on the total weight of the composition.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Making up" as used herein means to provide decoration (for example, color) to the nail.

"Protecting" as used herein means to inhibit damage to the nail (for example, chipping) by providing a protective layer on the nail.

"Nails", "fingernail or "toenail" refers to a human keratinous substrate on a finger or toe which can be treated (decorated) with a single or multiple nail cosmetic compositions.

"Nail treatment system" or "nail composition set" means multiple compositions applied on the surface of nails.

"Nail composition" or "lacquer" or "nail polish" or "nail enamel" or "nail coating" or "nail film" refers to nail enamel usable as a basecoat, color coat, top coat, clear coat and protective coat applied on nails separately and/or as a combined application of the above.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Gloss" in compositions as used herein refers to compositions having with an average gloss, measured at 20°, of greater than or equal to 35, for example 40, preferably 45, 55, 60 or 65, including all ranges and subranges therebetween such as 35-65, 40-65, etc., and/or an average gloss, measured at 60°, of greater than or equal to 65, 70, 75 or 80, including all ranges and subranges therebetween such as 65-80, 65-75, etc.

The term "average gloss" denotes the gloss as it can be measured using a gloss meter, for example by spreading a layer of the composition to be tested, between 50 µm and 150 µm in thickness, on a white Leneta contrast card using an automatic spreader. The deposit is cured under UV-LED lamp for 1 min. The residual tacky layer is wiped off with lint free cotton saturated in alcohol solvent, and then the gloss is measured at 20° using a Byk Gardner gloss meter of reference microTRI-GLOSS. This measurement is repeated at least three times, and the average gloss in GU (gloss units) is the average of the at least three measurements carried out.

The average gloss at 60° is measured in a similar manner, the measurement being carried out at 60° rather than 20°.

"Shine enhancing agent" or "shine increasing agent" in accordance with the present invention means increasing shine or, as the case may be, mitigating or reducing any reduction in shine that may result from the use of corresponding amounts of non-shine enhancing materials.

"Water resistance" as used herein, means resistance of a material (substance) to the penetration of water, which may cause degradation of that material. The method implemented if assessment of this invention is further disclosed The compositions and methods of the present invention can comprise, consist of, or consist essentially of the essential elements and limitations of the invention described herein, as well as any additional or optional ingredients, components, or limitations described herein or otherwise useful.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

Silicone-Organic Polymer Hybrid Compound

In accordance with the present invention, nail compositions comprising at least one silicone-organic polymer hybrid compound are provided. Preferably, the at least one silicone-organic polymer hybrid compound is selected from a silicone vinyl acetate compound and a crosslinked anionic copolymer comprised of organic polymer blocks and silicone blocks, resulting in a multiblock polymer structure, or mixtures thereof.

In particular, suitable examples of the silicone-organic polymer hybrid compound of the present invention include, but are not limited to, copolymers of vinyl acetate and vinylsilicone. Such copolymers may optionally further include C3-7 carboxylic acid and/or vinyl C7-45 alkyl ester monomers.

In particular, suitable examples of the silicone-organic polymer hybrid compound of the present invention include, but are not limited to, crosslinked anionic copolymers comprising at least one crosslinked polysiloxane structural unit. PCT patent application publication no. WO 2011/069786, the entire contents of which is hereby incorporated by reference, discloses such compounds.

A preferred silicone-organic polymer hybrid compound of the present disclosure is a compound having the INCI name of Crotonic Acid/Vinyl C8-12 Isoalkyl Esters/VA/Bis-Vinyldimethicone Crosspolymer which is a copolymer of Crotonic Acid, vinyl C8-12 isoalkyl esters and Vinyl Acetate crosslinked with bis-vinyldimethicone. This compound is commercially available from the company Wacker Chemie AG under the tradename Wacker Belsil®P1101 (may also be known under the tradename Wacker Belsil® P101). Crotonic Acid/Vinyl C8-12 Isoalkyl Esters/VA/Bis-Vinyldimethicone Crosspolymer is also known by the technical name of Crotonic AcidNinyl C8-12 Isoalkyl Esters/VA/divinyldimethicone Crosspolymer.

Preferably, the at least one silicone-organic polymer hybrid compound is present in the nail composition of the present invention in amounts of active material generally ranging from about 2% to about 20%, preferably from about 3% to about 15%, and more preferably from about 5% to about 11%, by weight, based on the total weight of the cosmetic composition, including all ranges and subranges in between.

Base Composition for the Nail Composition

According to preferred embodiments, the base composition for the nail compositions of the present invention is a UV gel composition. Examples of such UV gel compositions include, but are not limited to, a photocrosslinkable composition such as disclosed in U.S. patent application publication no. 2015/0306013 (the entire content of which is hereby incorporated by reference) and a fast-curing composition such as disclosed in U.S. patent application publication no. 2015/0139924 (the entire content of which is hereby incorporated by reference). Set forth below are examples of ingredients which can be found in the nail compositions of the present invention, although all of the identified ingredients need not be present.

Photocrosslinkable Compound

According to preferred embodiments, the nail compositions of the present invention comprise at least one photocrosslinkable compound. The term "photocrosslinkable compound" refers to an organic compound suitable for crosslinking under the action of a light ray and/or UV rays, resulting in a crosslinked polymer network.

Preferably, the photocrosslinkable compound(s) and silicone-organic polymer hybrid compound(s) are present in the nail compositions of the present invention in a photocrosslinkable compound to silicone-organic polymer hybrid compound weight ratio of from 5:1 to 1:2.5, preferably from 4:1 to 1:2, preferably from 3.5:1 to 1:1.5, and preferably from 3.5:1 to 1:1, including all ranges and subranges therebetween. According to preferred embodiments of the present invention, compositions of the present invention contain more photocrosslinkable compound than silicone-organic polymer hybrid compound by weight.

Urethane (meth)acrylate Compound

According to preferred embodiments, the photocrosslinkable compound is at least one photocrosslinkable urethane (meth)acrylate compound. The term "urethane (meth)acrylate compound" refers to any compound comprising at least one urethane function —O—C(O)—NH—, also known as a carbamate, and at least one (meth)acrylate function according to the formula

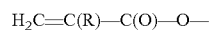

where R=H or $CH_3$.

The "urethane" function is also referred to as a "carbamate" function. The urethane (meth)acrylate compound may be chosen from the group consisting of urethane poly(meth)acrylate compounds. According to the present invention, the term "poly(meth)acrylate compound" refers to a (meth)acrylate compound comprising a plurality of (meth)acrylate functions.

In this way, the term "poly(meth)acrylate compound" may refer to a compound comprising at least two methacrylate functions, or at least two acrylate functions, or at least one methacrylate function and at least one acrylate function.

As urethane (meth)acrylate compounds, particular mention may be made of urethane dimethacrylate compounds.

The term "urethane dimethacrylate compound" refers to any compound comprising at least one urethane function —O—C(O)—NH—, and two methacrylate functions according to the formula

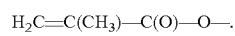

The term "polyurethane group" refers to a group obtained from polymerizing a mixture of monomers comprising isocyanate functions and monomers.

Particularly preferred urethane (meth)acrylate compounds are those commercially available from Esstech, Inc. (www.esstechinc.com) under the name Exothane such as, for example, Exothane 8, Exothane 9, Exothane 10, Exothane 24, Exothane 26, Exothane 32, Exothane 108, and Exothane 126. The Exothane compounds are elastomers having high conversion values properties leading to improved adhesion. For example, preferred compounds have conversion values of 80% or greater, preferably 85% or greater, preferably 90% or greater, including all ranges and subranges therebetween such as, for example, 83% to 99%, 85% to 99%, 90% to 99%, etc. Further, such compounds preferably have high viscosity, preferably between 8,500 cPs and 1,000,000, preferably between 10,000 cPs and 900,000 cPs, and preferably between 20,000 and 850,000 cPs at 25° C., including all ranges and subranges therebetween. Further, such compounds preferably have low shrinkage stress (MPa), preferably 1.0 or less, preferably 0.5 or less, preferably 0.3 or less, preferably 0.2 or less, including all ranges and subranges therebetween. Further, such compounds preferably have high elongation properties, preferably at least 10%, preferably at least 20%, preferably at least 30%, preferably at least 50%, and as high as 100% or higher, including all ranges and subranges therebetween such as, for example, 10% to 100%, 20% to 100%, etc. Further, such compounds preferably have low tensile strength (N/mm²), preferably less than 30 N/mm², preferably less than 25 N/mm², and preferably less than 20 N/mm².

The at least one photocrosslinkable urethane (meth)acrylate compound is preferably present at a total content greater than or equal to 1% by weight, in relation to the total weight of the composition, advantageously ranging from about 1% to about 80%, preferably from about 5% to about 75%, more preferably from about 10% to about 70%, advantageously from about 25% to about 65% by weight in relation to the total weight of the composition.

(Meth)acrylate Monomer (Ethylenically Unsaturated Monomer)

According to preferred embodiments, the photocrosslinkable compound is at least one photocrosslinkable (meth) acrylate monomer. (Meth)acrylate monomer refers to a compound comprising a single (meth)acrylate function according to the formula $H_2C=C(R)-C(O)-O-$, where $R=H$ or $CH_3$ capable of reacting with other molecules. In various embodiments, the at least one (meth)acrylate monomer may have a molecular weight ranging from 100 to about 300, for example, from about 120 to about 250.

In various embodiments, the at least one (meth)acrylate monomer may be chosen from compounds of general formula (I):

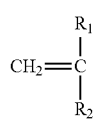

wherein:
- $R_1$ is chosen from hydrogen and $C_1$-$C_{30}$ alkyl radicals and $R_2$ is chosen from —COOM radicals, wherein M is chosen from $C_1$-$C_{30}$ straight or branched chain alkyl radicals optionally substituted with at least one hydroxyl group or heterocycle, and from polyalkyleneoxy groups comprising preferably from 2 to 4 units, and from aromatic, alicyclic, and bicyclic rings optionally substituted with at least one substituent chosen from $C_1$-$C_{30}$ straight or branched chain alkyl radicals which may be substituted with at least one hydroxyl group. In another embodiment, the at least one (meth) acrylate monomer may be chosen from monomers of formula (I), wherein $R_1$ is chosen from hydrogen and $CH_3$, and
- $R_2$ is chosen from —COOM radicals, wherein M is chosen from $C_1$-$C_{10}$ straight or branched chain alkyl radicals optionally substituted with at least one hydroxyl group or heterocycle, and from aromatic, alicyclic, and bicyclic rings optionally substituted with at least one substituent chosen from $C_1$-$C_{30}$ straight or branched chain alkyl radicals which may be substituted with at least one hydroxyl group.

For example, the (meth)acrylate monomer may be chosen from (meth)acrylate monomers, such as methyl (meth)acrylate (MMA), ethyl (meth)acrylate (EMA), butyl (meth) acrylate (BMA), and polyethylene monomethacrylate such as diethylene glycol monomethacrylate, polypropylene glycol monomethacrylate such as dipropylene glycol monomethacrylate, and isobornyl (meth)acrylate, and tetrahydrofurfuryl (meth)acrylate (THFMA), and hydroxyalkyl (meth)acrylate monomers, such as hydroxypropyl methacrylate (HPMA), hydroxyethyl (meth)acrylate (HEMA), and butoxyethyl (meth)acrylate (BEMA).

Particularly useful for this invention is tetrahydrofurfuryl methacrylate (THFMA) available from Esstech, Inc. (X-958-7466).

Preferably, the (meth)acrylate monomer is present in the composition of the invention in the amount from about 0.01% to about 60% by weight, typically from about 5% to about 30% by weight, more particularly from about 10% to about 26% by weight, including all ranges and subranges there between, all weights being based on the total weight of the composition.

Film Forming Polymer

According to preferred embodiments, the nail compositions of the present invention comprise at least one non-photocurable film forming polymer. "Film-forming polymer" refers to a non-photocurable polymer suitable for forming alone (i.e. in the absence of an auxiliary film-forming agent or an external stimulus for example such as UV rays), a film suitable for being isolated, particularly a continuous adherent film, on a substrate, particularly on nails. Preferably, the film forming polymer is selected from the group consisting of radical or polycondensate type synthetic polymers, polymers of natural origin, and mixtures thereof.

Specific examples of suitable film forming polymers include, but are not limited to, polysaccharide derivatives, such as cellulose or guar gum derivatives including nitrocellulose and/or a polysaccharide ester or alkylether such as a polysaccharide consisting of repeat units comprising at least two identical or different rings and having a degree of substitution per saccharide unit between 1.9 and 3, preferably between 2.2 and 2.9, and preferably between 2.4 and 2.8, such as cellulose esters (such as cellulose acetobutyrates or cellulose acetopropionates), cellulose alkylethers (such as ethylcelluloses), and ethylguars.

Specific examples of suitable film forming polymers also include, but are not limited to, polyurethanes, polyvinylbutyrals, and ketone/aldehyde resins, resins from aldehyde condensation products, such as aryl sulfonamide formaldehyde resins such as toluene sulfonamide formaldehyde resin, aryl-sulfonamide epoxy resins or ethyl tosylamide resins.

Preferably, the at least one film forming polymer is present in the nail composition of the present invention in amounts of active material generally ranging from about 2% to about 60%, preferably from about 5% to about 50%, and more preferably from about 8% to about 45%, by weight, based on the total weight of the cosmetic composition, including all ranges and subranges in between.

Photoinitiator

According to preferred embodiments, the nail compositions of the present invention comprise at least one photoinitiator. The photoinitiators suitable for use include those described, for example in "Les photoinitiateurs dans la reticulation des rev tements", G. Li Bassi, Double Liaison—Chimie des Peintures, No. 361, November 1985, p. 34-41; "Applications industrielles de la polymerisation photoinduite", Henri Strub, L'Actualite Chimique, February 2000, p. 5-13; and "Photopolymeres: considerations theoriques et reaction de prise", Marc, J. M. Abadie, Double Liaison-Chimie des Peintures, No. 435-436, 1992, p. 28-34.

Suitable photoinitiators include, but are not limited to, alpha-hydroxyketones, marketed for example under the names DAROCUR® 1173 and 4265, IRGACURE® 184, 2959, and 500 by BASF, and ADDITOL® CPK by CYTEC, alpha.-aminoketones, marketed for example under the names IRGACURE® 907 and 369 by BASF, aromatic ketones marketed for example under the name ESACURE® TZT by LAMBERTI, thioxanthones marketed for example under the name ESACURE® ITX by LAMBERTI, and quinones (these aromatic ketones generally require the presence of a hydrogen donor compound such as tertiary amines and particularly alkanolamines—mention may particularly be made of the tertiary amine ESACURE® EDB marketed by LAMBERTI), alpha-dicarbonyl derivatives of which the most common is benzyl dimethyl ketal marketed under the name IRGACURE® 651 by BASF, and acylphosphine oxides, such as for example bis-acylphosphine oxides (BAPO) marketed for example under the names IRGACURE® 819, 1700, and 1800, DAROCUR® 4265, LUCIRIN® TPO, and LUCIRIN® TPO-L by BASF. Preferably, the photoinitiator is selected from the group consisting of alpha-hydroxyketones, alpha-aminoketones, aromatic ketones preferably associated with a hydrogen donor compound, aromatic alpha-diketones, acylphosphine oxides, and mixtures thereof.

Preferably, the at least one photoinitiator is present in the nail composition of the present invention in amounts of active material generally ranging from about 0.1% to about 10%, preferably from about 1% to about 7%, and more preferably from about 2.5% to about 5%, by weight, based on the total weight of the cosmetic composition, including all ranges and subranges in between.

Solvent

According to preferred embodiments, nail compositions further comprising at least one solvent are provided. Any solvent typically found in nail polish compositions can be used. Suitable solvents include, but are not limited to, organic solvents which are liquid at ambient temperature. Examples of suitable solvents include, but are not limited to, ketones such as methyl ethyl ketone, methyl isobutyl ketone, diisobutyl ketone, isophorone, cyclohexanone or acetone; alcohols, such as ethanol, isopropanol, diacetone alcohol, 2-butoxyethanol or cyclohexanol; glycols, such as ethylene glycol, propylene glycol, pentylene glycol or glycerol; propylene glycol ethers, such as propylene glycol monomethyl ether, propylene glycol monomethyl ether acetate or dipropylene glycol mono(n-butyl) ether; short-chain esters (having a total of 2 to 7 carbon atoms), such as ethyl acetate, methyl acetate, propyl acetate, n-butyl acetate or isopentyl acetate; alkanes, such as decane, heptane, dodecane or cyclohexane; and their mixtures. Most preferred are short-chain esters (having a total of from 2 to 8 carbon atoms).

Preferably, if present, the at least one solvent is present in the nail composition of the present invention in amounts of active material generally ranging from about 0.1% to about 50%, preferably from about 5% to about 40%, and more preferably from about 10% to about 35%, by weight, based on the total weight of the cosmetic composition, including all ranges and subranges in between.

Colorant

According to preferred embodiments, nail compositions further comprising at least one colorant are provided. Any colorant typically found in nail polish compositions can be used. Suitable colorants include, but are not limited to, lipophilic dyes, pigments, pearlescent agents, glitter, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

Preferably, if present, the at least one colorant is present in the nail composition of the present invention in amounts of active material generally ranging from about 0.1% to about 10%, preferably from about 0.25% to about 7%, and more preferably from about 0.5% to about 3.5%, by weight, based on the total weight of the cosmetic composition, including all ranges and subranges in between.

Auxiliaries/Additives

The nail compositions of the present invention may additionally comprise an additive or auxiliary commonly used in cosmetic compositions and known to a person skilled in the art as being capable of being incorporated into a nail polish or varnish composition. Such additives or auxiliaries may be chosen from gelling agents, thickeners, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

In particular, among the gelling agents that may be used, mention may be made of lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

In particular, among the gelling agents that may be used, mention may be made of silica particles. Preferably, the silica particles are fumed silica particles.

Suitable silicas include, but are not limited to, hydrophobic silicas, such as pyrogenic silica optionally with hydrophobic surface treatment whose particle size is less than 1 micron, preferably less than 500 nm, preferably less than 100 nm, preferably from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-0-SIL TS-720®" by the company Cabot.

Preferably, the gelling agent, if present, is present in the nail composition of the present invention in amounts of active material generally ranging from about 0.1% to about 10%, preferably from about 0.25% to about 5%, and more preferably from about 0.5% to about 3.5%, by weight, based on the total weight of the cosmetic composition, including all ranges and subranges in between.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

Nail Composition Set

According to the present invention, a nail composition set comprising at least one color coat and at least one basecoat are provided. The nail composition set of the present invention can optionally further comprise at least one primer coat and/or at least one topcoat.

For example, a nail composition set comprising at least one primer, at least one basecoat, at least one color coat and at least one topcoat are provided. However, the primer coat and/or topcoat are optional. Thus, nail composition sets comprising at least one primer, at least one basecoat and at least one color coat, as well as nail composition sets comprising at least one basecoat, at least one color coat and at least one topcoat are provided by the present invention.

It should be understood that each coat or layer in the nail composition set, itself, can comprise one or more layers of each composition. Thus, the at least one primer can comprise one or more primer layers; the at least one basecoat can comprise one or more basecoat layers; the at least one color coat can comprise one or more color coat layers; and the at least one topcoat can comprise one or more topcoat layers. Preferably, each primer, basecoat, color coat and topcoat contains three or fewer layers or compositions, more preferably two or fewer layers or compositions, and most preferably a single layer or composition.

According to the present invention, at least one composition of the nail composition set is a nail composition comprising at least one silicone-organic polymer hybrid compound in accordance with the present invention. The other composition(s) of the nail composition set may be any suitable composition for application to nails. For example, the basecoat(s) can be an adhesive layer or an undercoat layer; the color coat(s) can be a nail polish composition(s) such as, for example, a standard UV gel composition; the topcoat(s) can be an extra shine layer and/or a protective layer, etc.

The present invention also relates to methods for improving gloss of a nail composition comprising (1) forming a nail composition comprising at least one silicone-organic polymer hybrid compound and (2) providing instructions (a) to apply the nail composition to nails to form an applied composition on the nails, (b) to subject the applied composition to ultraviolet (UV) or visible light radiation to form a cured composition on the nails, and (c) to apply at least one short chain alcohol to the cured composition on the nails in an amount sufficient to increase gloss of the cured composition. According to these methods, the short chain alcohol is preferably a C3-C5 alcohol, and the short chain alcohol is preferably branched. Isopropyl alcohol is most preferred. Further according to these methods, the short chain alcohol is applied to the cured composition by saturating a carrier substrate such as a cloth, cotton swab or cotton ball a wiping or rubbing the cured composition with the saturated carrier substrate. Also according to these methods, at least one consumer (for example, either the person on whose nails the compositions are applied and/or the person who applies the compositions to nails) is provided the instructions discussed above.

The present invention also relates to methods for improving gloss of a nail composition comprising (1) forming a nail composition comprising at least one silicone-organic polymer hybrid compound and (2) providing instructions (a) to apply the nail composition to nails to form an applied composition on the nails, (b) to subject the applied composition to ultraviolet (UV) or visible light radiation to form a cured composition on the nails, and (c) to apply at least one short chain alcohol to the cured composition on the nails, resulting in a glossy cured composition. According to these methods, the short chain alcohol is preferably a C3-C5 alcohol, and the short chain alcohol is preferably branched. Isopropyl alcohol is most preferred. Further according to these methods, the short chain alcohol is applied to the cured composition by saturating a carrier substrate such as a cloth, cotton swab or cotton ball a wiping or rubbing the cured composition with the saturated carrier substrate to substantially remove a tacky layer. Also according to these methods, at least one consumer (for example, either the person on whose nails the compositions are applied and/or the person who applies the compositions to nails) is provided the instructions discussed above.

The present invention also relates to methods for improving gloss of a nail composition comprising (1) applying a nail composition comprising at least one silicone-organic polymer hybrid compound to nails to form an applied composition on the nails, subjecting the applied composition to ultraviolet (UV) or visible light radiation to form a cured composition on the nails, and applying at least one short chain alcohol to the cured composition on the nails, resulting in a glossy cured composition. According to these methods, the short chain alcohol is preferably a C3-C5 alcohol, and the short chain alcohol is preferably branched. Isopropyl alcohol is most preferred. Further according to these methods, the short chain alcohol is applied to the cured composition by saturating a carrier substrate such as a cloth, cotton swab or cotton ball a wiping or rubbing the cured composition with the saturated carrier substrate to substantially remove a tacky layer.

In association with the preceding methods of improving gloss, it has been surprisingly discovered that applying (for example, rubbing or wiping) a short chain alcohol such as isopropyl alcohol to or against the cured composition improves gloss without affecting materially affecting properties such as adhesion and water-resistance. Although not wishing to be bound by any particular theory, it is believed that application of the short chain alcohol effects removal of a tacky layer of the cured composition (due to oxygen inhibition of the free radical polymerization at the air surface interface), resulting in improved gloss properties.

Also in association with the preceding methods of improving gloss, for purposes of the methods of the present invention where the invention "consists essentially of" the identified ingredients and/or process steps, the sole "basic and novel property" of such methods is gloss. Further, given that it is contemplated that other gloss enhancers or boosters can be added to the invention methods in the context of the present invention, a "material effect" on the basic and novel property of the invention can only be an adverse effect. That is, because positive effects on gloss value (such as those effected by gloss enhancing agents) are within the scope of the present invention, only ingredients which have a material adverse effect on gloss value would be relevant to determining whether or not compositions or methods "consist essentially of" the required elements.

According to preferred embodiments of the present invention, methods of making up or protecting nails comprising applying to the nails at least one nail composition comprising at least one silicone-organic polymer hybrid compound to nails in an amount sufficient to makeup or protect the nails are provided.

According to preferred embodiments of all method claims discussed above, such methods comprise a) applying at least one coating of a nail composition of the present invention onto a nail or onto a previously applied composition on a nail (for example, primer), and b) exposing the coated nail to UV or visible light radiation, whereby photocrosslinking of at least one photocrosslinkable compound occurs.

Suitable radiation crosslinking the photocrosslinkable compound has, for example, a wavelength ranging from 210 to 600 nm, preferably from 250 to 420 nm, preferably from 350 to 410 nm. The use of lasers may also effect crosslinking. In one preferred embodiment of the invention methods, a LED lamp or an UV lamp, preferably a mercury vapor lamp, optionally doped with further elements, such as gallium, suitable for modifying the emission spectrum of the light source, can be used. Of course, the exposure time of the deposited coat to radiation is dependent on various factors such as the chemical nature and content of the reactive compounds or the crosslinking density sought. Typically, satisfactory results can be obtained after an exposure time ranging from 10 seconds to 100 minutes, preferably from 30 seconds to 5 minutes.

Before the crosslinking occurs but after application of the nail composition of the present invention, there may be a period for drying the deposited coated layer, the duration of which may vary from 10 seconds to 10 minutes, typically from 30 seconds to 3 minutes. The drying is generally performed in air and at ambient temperature.

According to preferred embodiments of the present invention, a kit for a nail composition set comprising at least one nail composition comprising at least one silicone-organic polymer hybrid compound and at least one additional composition selected from the group consisting of a primer, a basecoat, a color coat and a top coat are also provided. Preferably, the kit further comprises one or more of the following: instructions for applying a nail composition of the present invention; instructions for removing a nail composition of the present invention; an abrasive material having a granulometry greater than or equal to 200 µm, preferably less than 300 µm, preferably from 220 µm to 280 µm; and/or a LED lamp or an UV lamp.

The compositions according to the invention can be manufactured by known processes used generally in the cosmetics or dermatological field.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1—Compositions And Testing For Compositions Containing Varying Amounts of Silicone-Organic Polymer Hybrid Compound The formulations in the table below were prepared. These compositions contained varying amounts of silicone-organic polymer hybrid compound. Specifically, five compositions were prepared having the following amounts of silicone-organic polymer hybrid compound: 0% (comparative composition); 3%; 5%, 10%; and 19%:

Such formulations can be prepared by combining all raw materials, and then mixing at 2750 rpm for 2 min in high speed a SpeedMixer™ from Flateck. If desired, the silicone-organic polymer hybrid compound can be neutralized before combination with the other ingredients.

Gloss was then determined using a gloss meter. For this determination, a layer of the composition to be tested was spread on a contrast card using an automatic spreader. The layer covered at least the white background of the card and cured for 60 seconds using an LED lamp. Then, the deposit was wiped with isopropanol. Then, gloss was measured at 20° on the white background using a Byk Gardner gloss meter of reference microTRI-GLOSS. This measurement was repeated 3 times, and the average gloss (in gloss units (GU)) is the average of the 3 measurements carried out.

Adhesion/Removal properties were also assessed. For this determination, 2 cm×2 cm squares of Vitronails® from IMS Inc. were buffed with OPI 280 grid buffer in 2 different directions, then 2 layers of UV nail gel were applied composition with a brush. Each layer was cured 60 s under UV-LED lamp and the last layer was wiped with isopropanol to remove the sticky layer. The samples were left to set at least overnight. Then, difficulty to remove the product from vitronail was assessed. The adhesion/removal properties were assessed from 1 to 5, where 5 meant very easy to remove and 1 very difficult.

Acetone removal properties were also assessed. For this determination, 1 nail spoon with 2 layers of UV nail gel composition applied with a brush was prepared. Each layer was cured 60 s under UV-LED lamp and the last layer was wiped with isopropanol to remove the sticky layer. Afterwards a ~1 cm×1 cm cotton saturated with 0.3 mL of acetone was placed on the coated spoon for 3 minutes with a 100 g weight. After removal of the cotton, the surface was visually assessed and then the operator tried to remove the film with a plastic cuticle pusher. The ease of removal was assessed from 1 to 5, where 5 meant very easy to remove and 1 very difficult.

Water-resistance was also determined. 2 nail spoons were coated with 2 layers of UV nail gel composition with a brush. Each layer was cured 60 seconds under a UV-LED lamp and the last layer was wiped with isopropanol to remove the tacky layer. Afterwards 1 spoon was immersed in 45° C. soapy water (soap ~12 g/L) for 20 min. Once removed from the water the film was compared to the non-immersed spoon (for properties such as shine, color, smoothness), then scratched with a quarter to assess the integrity of the wet film. The water resistance was rated from 1 to 5 where 5 was very good water resistance and 1 was very poor water resistance.

The results are set forth in Table 1 below.

TABLE 1

| INCI name | Comparative | Invention formulas | | | |
|---|---|---|---|---|---|
| BIS-HEMA IPDI | 27.46 | 27.46 | 27.46 | 27.46 | 27.46 |
| DI-HEMA TRIMETHYLHEXYL DICARBAMATE | 6.87 | 6.87 | 6.87 | 6.87 | 6.87 |
| TETRAHYDROFURFURYL METHACRYLATE | 14.30 | 14.30 | 14.30 | 14.30 | 14.30 |
| HEMA MALEATE | 8.58 | 8.58 | 8.58 | 8.58 | 8.58 |
| Crotonic acid/vinyl C8-12 isoalkyl esters/VA/bis-vinyl-dimethicone crosspolymer | 0.00 | 3.00 | 5.00 | 10.00 | 19.10 |
| Ethanol | | 3.00 | 5.00 | 10.00 | 19.10 |
| ETHYL TRIMETHYLBENZOYL PHENYLPHOSPHINATE | 4.00 | 4.00 | 4.00 | 4.00 | 4.00 |
| Red 6 Lake | 0.24 | 0.24 | 0.24 | 0.24 | 0.24 |
| Red 7 Lake | 0.29 | 0.29 | 0.29 | 0.29 | 0.29 |
| TITANIUM DIOXIDE (and) OXIDIZED POLYETHYLENE | 0.10 | 0.10 | 0.10 | 0.10 | 0.10 |
| ETHYL ACETATE | 38.16 | 32.16 | 28.16 | 18.16 | 0.00 |
| Total | 100.0 | 100.0 | 100.0 | 100.0 | 100.0 |
| Gloss @ 20° (GU) | 42.7 ± 0.4 | 55.2 ± 1.4 | 66.0 ± 1.0 | 65.3 ± 1.2 | 60.8 ± 0.3 |
| Water resistance (2 coats) | 1.5 | 1.5 | 1.5 | 2.5 | 2.5 |
| Adhesion to Vitronails ® | 5 ± 0.5 | 5 ± 0.5 | 4.75 ± 0.5 | 4.5 ± 0.5 | 4.25 ± 0.5 |
| Acetone removal | 3 ± 0.5 | 3 ± 0.5 | 3.5 ± 0.5 | 4.5 ± 0.5 | 4.5 ± 0.5 |

According to the results in Table 1, adding silicone-organic polymer hybrid compound clearly improves the shine of the original UV nail gel system (as compared to the comparative composition, particularly at amounts of 5% and greater.

Moreover, this higher shine was achieved while preserving good adhesion and good solvent removal properties.

Using the same protocol as described above, a commercially available product which did not contain silicone-organic polymer hybrid compound was obtained and tested. The results in Table 2 demonstrate that that commercially available product possessed inferior properties as compared to the present invention.

TABLE 2

|  | Commercially Available Product Lacking Silicone-Organic Polymer Hybrid Compound (Haute) |
|---|---|
| Gloss @ 20° (GU) | 30.5 ± 0.1 |
| Water resistance (2 coats) | 2.5 |
| Adhesion to Vitronails ® | 1 ± 0.5 |
| Acetone removal | 3.5 ± 0.5 |

What is claimed is:

1. A method for improving gloss of a nail composition comprising: applying a nail composition comprising 0.1% to 50% by weight of at least one volatile solvent and at least 5% by weight of at least one silicone-organic polymer hybrid compound, wherein the silicone-organic polymer hybrid compound is a copolymer of a vinyl acetate, a vinylsilicone, a C3-7 carboxylic acid and a vinyl C7-45 alkyl ester, all weights being based on the total weight of the nail composition, to nails to form an applied composition on the nails; subjecting the applied composition to ultraviolet (UV) or visible light radiation to form a cured composition on the nails; and applying at least one a C3-C5 alcohol to the cured composition on the nails, resulting in a glossy cured composition.

2. The method of claim 1, wherein the C3-C5 alcohol is isopropyl alcohol.

3. The method of claim 1, wherein the silicone-organic polymer hybrid compound is present in an amount ranging from 5% to 20% by weight with respect to the weight of the composition.

4. The method of claim 1, wherein the glossy cured composition has a gloss, measured at 20°, of greater than or equal to 60 GU.

5. The method of claim 1, wherein the at least one volatile solvent is present in the nail composition in an amount ranging from about 5% to about 40% by weight based upon the total weight of the nail composition.

6. The method of claim 1, wherein the at least one volatile solvent is present in the nail composition in an amount ranging from about 10% to about 35% by weight based upon the total weight of the nail composition.

7. A method for improving gloss of a nail composition comprising: applying a nail composition comprising 0.1% to 50% by weight of at least one volatile solvent and at least 5% by weight of at least one silicone-organic polymer hybrid compound, wherein the silicone-organic polymer hybrid compound is Crotonic Acid/Vinyl C8-12 Isoalkyl Esters/VA/Bis-Vinyldimethicone Crosspolymer, all weights being based on the total weight of the nail composition, to nails to form an applied composition on the nails; subjecting the applied composition to ultraviolet (UV) or visible light radiation to form a cured composition on the nails; and applying at least one a C3-C5 alcohol to the cured composition on the nails, resulting in a glossy cured composition.

8. The method of claim 7, wherein the C3-C5 alcohol is isopropyl alcohol.

9. The method of claim 7, wherein the silicone-organic polymer hybrid compound is present in an amount ranging from 5% to 20% by weight with respect to the weight of the composition.

10. The method of claim 7, wherein the glossy cured composition has a gloss, measured at 20°, of greater than or equal to 60 GU.

11. The method of claim 7, wherein the at least one volatile solvent is present in the nail composition in an amount ranging from about 5% to about 40% by weight based upon the total weight of the nail composition.

12. The method of claim 7, wherein the at least one volatile solvent is present in the nail composition in an amount ranging from about 10% to about 35% by weight based upon the total weight of the nail composition.

* * * * *